US006973162B2

(12) United States Patent
Block et al.

(10) Patent No.: US 6,973,162 B2
(45) Date of Patent: Dec. 6, 2005

(54) MR/X-RAY SCANNER HAVING ROTATABLE ANODE

(75) Inventors: Wayne F. Block, Sussex, WI (US); J. Scott Price, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 180 days.

(21) Appl. No.: 10/605,844

(22) Filed: Oct. 30, 2003

(65) Prior Publication Data

US 2005/0096532 A1    May 5, 2005

(51) Int. Cl.[7] .......................................... G01N 23/04
(52) U.S. Cl. ........................ 378/63; 600/411; 600/427
(58) Field of Search ......................... 378/63; 600/411, 600/427

(56) References Cited

U.S. PATENT DOCUMENTS

| | | | | |
|---|---|---|---|---|
| 3,456,175 A | * | 7/1969 | Bavor | 378/125 |
| 3,942,059 A | * | 3/1976 | Tran-Quang | 378/128 |
| 4,162,420 A | * | 7/1979 | Grady | 378/126 |
| 4,377,002 A | * | 3/1983 | Krause et al. | 378/93 |
| 5,339,348 A | * | 8/1994 | Wirth et al. | 378/93 |
| 5,574,417 A | * | 11/1996 | Dorri et al. | 335/216 |
| 5,873,825 A | * | 2/1999 | Mistretta et al. | 600/410 |
| 6,211,677 B1 | * | 4/2001 | Burl et al. | 324/322 |
| 6,798,118 B1 | * | 9/2004 | Wen | 310/323.02 |
| 2003/0123612 A1 | * | 7/2003 | Pelc et al. | 378/137 |

OTHER PUBLICATIONS

Prager, R., Cambridge University Engineering Tripos Part IIB, Module I9; Medical Image Acquisition, Handout 1: X-Rays and the Radon Transform, Jan. 2002, pp. 1-21.
Fahrig, R. et al., A Truly Hybrid Interventional MR/X-Ray System: Feasibility Demonstration, Journal of Magnetic Resonance Imaging, 2001, vol. 13, pp. 294-300.
Vogl, T. et al., Hybrid MR Interventional Imaging System: Combined MR and Angiography Suites With Single Interactive Table. Feasibility Study in Vascular Liver Tumor Procedures, European Radiology, 2002, vol. 12, pp. 1394-1400.

* cited by examiner

*Primary Examiner*—Allen C. Ho
*Assistant Examiner*—Chih-Cheng Glen Kao
(74) *Attorney, Agent, or Firm*—Ziolkowski Patent Solutions Group, SC; Michael A. Della Penna; Carl B. Horton

(57) ABSTRACT

A hybrid MR/x-ray scanner is disclosed that allows for the acquisition of x-ray as well as MR data in a single exam without requiring patient repositioning. As an MR scanner, the hybrid system is capable of providing images with soft tissue contrast, excellent 3D visualization, the ability to image in multiple scan planes, as well as the possibility of providing physiological information. The x-ray components of the hybrid scanner include a rotatable anode that rotates during data acquisition and is caused to rotate without introduction of unwanted magnetic flux to the MR magnetic field.

13 Claims, 2 Drawing Sheets

MR/X-RAY SCANNER HAVING ROTATABLE ANODE

BACKGROUND OF INVENTION

The present invention relates generally to diagnostic imaging systems and, more particularly, to a combined magnetic resonance (MR) and x-ray scanner having a rotatable anode.

A number of diagnostic imaging systems have been developed to assist physicians, radiologists, other healthcare providers, and researchers with non-invasive or minimally invasive detection and treatment of anatomical abnormalities and pathologies. These imaging systems include x-ray radiography, computed tomography (CT), single proton emission computed tomography (SPECT), positron emission tomography (PET), ultrasound, magnetic resonance imaging (MRI), and derivatives of each. Each of these diagnostic imaging systems, as well as other not specifically enumerated, are used to produce medical or other clinically valuable images based on the detection and processing of energy through a subject. Radiography was the first developed medical imaging technology and is predicated upon the projection of x-rays emitted by an x-ray tube toward a subject. A homogeneous distribution of x-rays then enters the subject and is modified by the degree to which the x-rays are removed from the beam by scattering and absorption within tissues in the subject. Since the attenuation properties of tissue, bone, soft tissue, and air inside the patient vary, a resulting heterogeneous distribution of x-rays emerges from the subject. This heterogeneous distribution of x-rays is detected by a typically flat x-ray detector on the other side of the subject and is used to generate a radiographic image of the heterogeneous distribution. The radiographic image is a picture of this heterogeneous x-ray distribution through the subject.

MRI is another diagnostic imaging technique or modality that uses magnetic fields that are approximately 10,000 to 60,000 times stronger than the earth magnetic field. When a substance such as human tissue is subjected to this extremely strong and uniform magnetic field, individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", in z, may be rotated, or "tipped", into the x-y plane to produce a net transverse magnetic moment $M_t$. A signal is emitted by the excited spins after the excitation signal $B_1$ is terminated and the signal may be received and processed to form an image.

When utilizing the signals to produce MR images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct an MR image using one of many well-known reconstruction techniques.

MRI produces a set of tomographic slices through the subject, where each point in the image is predicated upon the micromagnetic properties of corresponding tissue at that point. Since different types of tissue such as fat, white and gray matter in the brain, cerebral spinal fluid, and cancers all have different local magnetic properties, images generated using MRI demonstrate high sensitivity to anatomical variations and are, therefore, typically high in contrast. As a result of this relatively high sensitivity to anatomical variations, MRI is frequently used in neurological imaging, muscle skeletal applications, as well as blood flow imaging.

As noted with respect to MRI, each diagnostic modality may be the preferred depending upon patient characteristics as well as the goal of the diagnostic imaging process. For example, radiographic or x-ray imaging is typically utilized for the detection of skeletal pathologies such as bone fractures. Since ultrasound is less harmful than ionizing radiation to a growing fetus, ultrasound imaging is typically preferred in obstetric patients. CT is often utilized for the detection of cancers, ruptured discs, subdural hematomas, aneurysms, as well as a large number of additional pathologies. Because of this relative independence between each of the imaging modalities, recent developments in diagnostic imaging system design have included the combination of multiple imaging modalities into a single scanner. For example, a hybrid MRI and a digital subtraction angiography scanner has been proposed wherein each imaging system is maintained in separate rooms that utilizes a single table for transferring patients between the imaging units. With this combined or hybrid system, standard clinical imaging as well as interventional procedures may be carried out with minimal repositioning of the patient. A drawback of this proposed hybrid system, however, is that two separate and independent scanners must be housed and maintained. That is, the independence of each scanner is maintained with a minimal interdependence of a common table to transfer the patient from the MR scanner to the angiographic system and vice-versa.

Another proposed hybrid system combines MR and x-ray in a single scanner. Such a scanner enables both x-ray fluoroscopy and MRI in a single exam without requiring patient repositioning as was typically required of combination or hybrid systems. With this proposed scanner, a flat panel x-ray detector is placed underneath the patient bed and a fixed anode x-ray tube is positioned overhead with the anode-cathode axis aligned with the main magnetic field and a high frequency x-ray generator. Since an MR system must maintain a very stable, uniform high magnetic flux field in order for the system to acquire accurate signals for image reconstruction, this hybrid MR/x-ray system referenced above implements a fixed or stationary anode. Typically, a stand-alone x-ray scanner utilizes a rotating anode. The anode is typically rotated using an induction motor. An induction motor, however, generates a magnetic flux that is disruptive to the substantially homogeneous magnetic field required for effective MR data acquisition and, therefore, would cause artifacts in the reconstructed image. A stationary, or fixed, anode, however, greatly reduces the x-ray dose available for radiographic data acquisition.

As is generally well known, the anode is a metal target electrode that is maintained at a positive potential difference relative to a cathode. Electrons striking the anode deposit most of their energy as heat with a small fraction emitted as x-rays. Consequently, the production of x-rays, in quantities necessary for acceptable image quality, generates a large amount of heat in the anode. With stationary, or fixed, anode configurations, a tungsten insert is embedded in a copper block. The copper block serves a dual role as support for the tungsten target as well as for removal of heat from the tungsten target. However, the small target area limits heat dissipation and consequently limits the maximum tube current and thus the x-ray flux. Rotating anodes, in contrast, have superior heat-loading characteristics and, consequently, higher x-ray output capabilities than stationary, or fixed, anode configurations. Electrons impart their energy on a continuously rotating target thereby spreading thermal energy over a large area and mass of the anode disc. Generally, an induction motor is used to rotate the anode during data acquisition. This rotation not only fans the x-ray beam, but also dissipates heat from the tungsten target across the surface and mass of the anode disc. As a result of these improved heat dissipating characteristics, the tube current for rotating anode configurations may be significantly greater than that typically used for stationary anode configurations. X-ray dose is directly proportional to the tube current and, as such, an increase in tube current provides an increase in available x-ray dosage for data acquisition. However, as noted above, typical rotating anode assemblies utilize an induction motor to induce rotation. The induction motor, however, generates a magnetic flux that would be disruptive to the homogeneous magnetic field required for MR data acquisition if incorporated in a conventional MR scanner. In this regard, a rotating anode configuration has been deemed impractical for a hybrid or combined MR/x-ray scanner.

It would, therefore, be desirable to design a hybrid MR/x-ray scanner having a rotatable anode that may be rotated during data acquisition without disrupting the substantially homogeneous magnetic field required for MR data acquisition. It would be further desirable to have such a hybrid scanner that does not require patient repositioning to acquire the respective types of diagnostic data.

SUMMARY OF INVENTION

The present invention is directed to an MR/x-ray scanner having a rotatable anode that overcomes the aforementioned drawbacks.

A hybrid MR/x-ray scanner is disclosed that allows for the acquisition of x-ray as well as MR data in a single exam without requiring patient repositioning. As an MR scanner, the hybrid system is capable of providing images with soft tissue contrast, excellent 3D visualization, the ability to image in multiple scan planes, as well as the possibility of providing physiological information. The x-ray capabilities of the single hybrid scanner include providing high resolution, real-time 2D projections with excellent contrast for the guidance and placement of catheters, stints, platinum coils, and other metallic devices. A number of interventional procedures may benefit from using the disclosed scanner for both x-ray and MR image generation. For example, transjugular intrahepatic portosystemic shunt is a common clinical procedure that is used to treat bleeding esophageal varices due to portal-venous hypertension. The chemoembolization of hepatic tumors may also benefit from the disclosed hybrid scanner. A number of other applications may also benefit from the hybrid MR/x-ray system disclosed. Those procedures include vascular applications, biliary drainages, abscess drainages, gallstone removal, precutaneous nephrostomy, and kidney stone removal. Other interventional procedures as well as minimally invasive procedures may also benefit from the present invention.

The disclosed MR/x-ray system includes a rotatable anode that is driven by a motor such that the relatively homogeneous magnetic field necessary for MR data acquisition is not disturbed during the acquisition of radiographic data. The rotating anode has greater heat loading and consequent higher x-ray output capabilities compared to that of a fixed, or stationary, anode.

Therefore, in accordance with one aspect of the present invention, an imaging system is disclosed that includes an MR imaging apparatus to acquire MR data of a subject as well as an x-ray imaging apparatus having a rotatable anode integrally disposed in the MR imaging apparatus to acquire radiographic data of the subject.

In accordance with another aspect of the present invention, an MR apparatus is disclosed that includes an MR imaging system having a plurality of gradient coils positioned about a bore of a magnet to impress a polarizing magnetic field and an RF transceiver system and an RF switch controlled by a pulse module to transmit RF signals to an RF coil assembly to acquire MR images. The MR apparatus further includes a motor assembly configured to control rotation of a rotatable anode disposed in the bore of the magnet.

According to another aspect of the present invention, a method of diagnostic imaging includes the steps of impressing a substantially homogeneous magnetic field about a subject and projecting high frequency electromagnetic energy at the subject. The method further includes the steps of rotating an anode of a high frequency electromagnetic energy tube assembly in the magnetic field during the projecting, and acquiring MR and radiographic data from the subject.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

A hybrid MR/x-ray scanner is disclosed. The scanner has a rotatable anode that is driven by a motor such that magnetic flux is not introduced into a relatively homogeneous $B_0$ magnetic field during data acquisition. The disclosed scanner enables both x-ray and MR data acquisition in a single exam without requiring patient repositioning.

Figure 1:
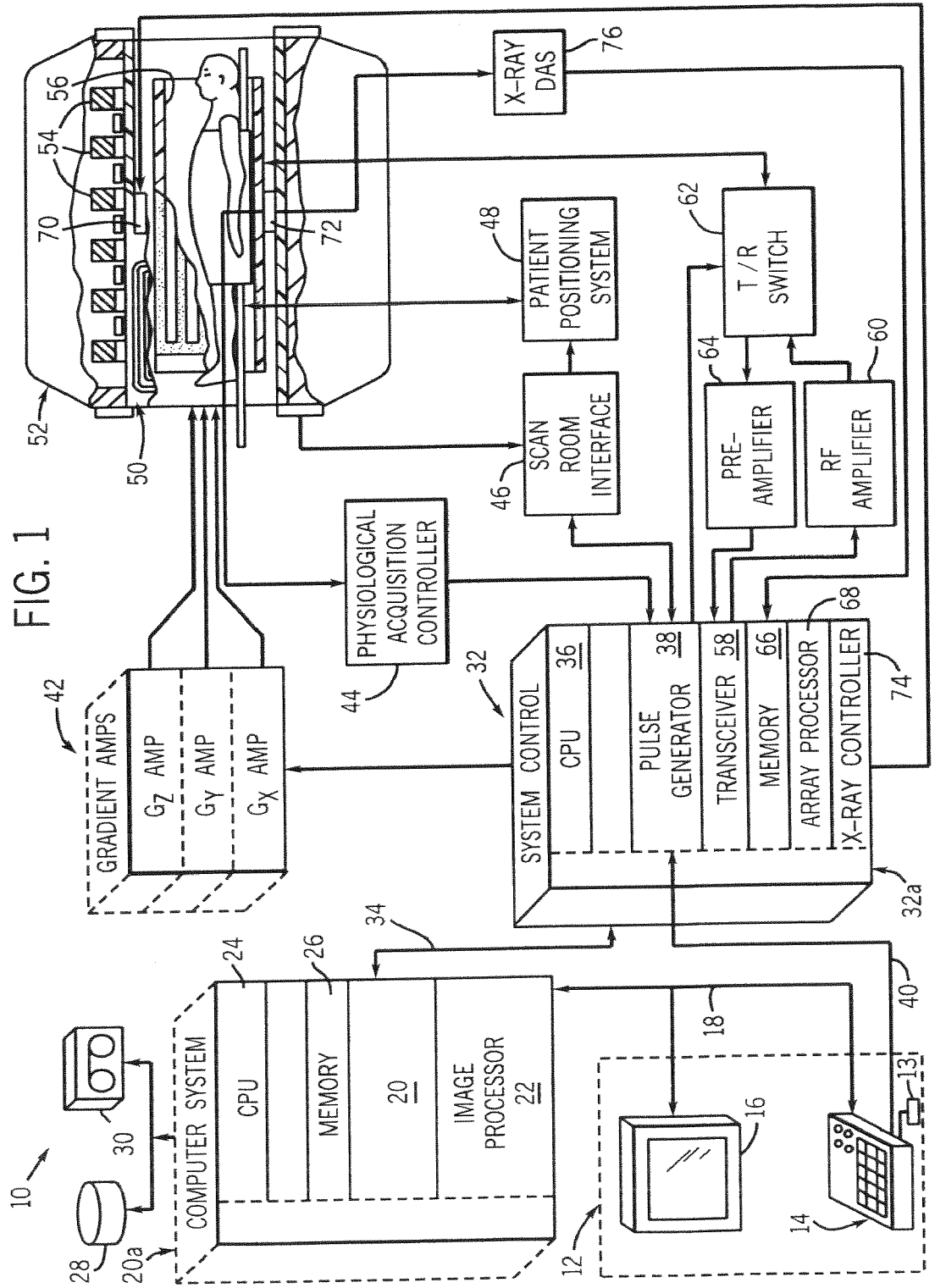
FIG. 1 is a schematic block diagram of a combined MR and x-ray imaging system for use with the present invention.

Referring to FIG. 1, the major components of a hybrid magnetic resonance imaging (MRI) and x-ray system 10 incorporating the present invention are shown. The operation of the MRI system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20*a*. These include an image processor module 22, a CPU module 24 and a memory module 26, known in the art as a frame buffer for storing image data arrays. The computer system 20 is linked to disc storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disc storage 28. In response to commands received from the operator console 12, this image data may be archived in long term storage, such as on the tape drive 30, or it may be further processed by the image processor 22 and conveyed to the operator console 12 and presented on the display 16.

Scanner 10 further includes an x-ray tube assembly 70 and detector assembly 72 for radiographic data acquisition. The x-ray tube assembly 70 is positioned within the bore of the magnet assembly 52 and includes a rotatable anode that is driven and controlled during data acquisition such that disturbances to the homogeneous magnetic field are avoided. Utilization of a rotating anode allows for increased x-ray dose availability relative to a stationary, or fixed, anode. Flat panel detector 72 is operationally connected to an x-ray data acquisition system 76 that is controlled by system control 32 or other central control. The system control includes an x-ray controller 74 designed to regulate operation of the x-ray components of the hybrid scanner.

Figure 2:
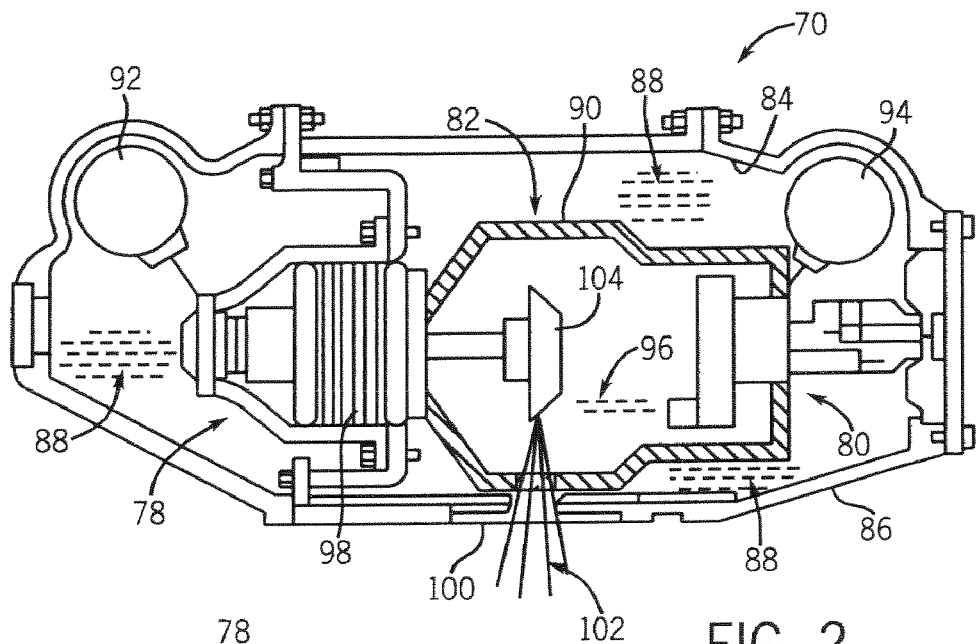
FIG. 2 is a cross-sectional view of an x-ray tube assembly.

Referring now to FIG. 2, components of x-ray tube assembly 70 are shown. The x-ray system 70 includes an anode 78 and a cathode 80 that collectively form an x-ray generating device or x-ray tube 82. A fluid chamber 84 is provided and housed within a lead-lined casing 86. Fluid chamber 84 is typically filled with coolant 88 that will be used to dissipate heat within the x-ray generating device 82. Coolant 88 is typically a dielectric oil, but other coolants including air may be implemented. An oil pump (not shown) circulates the coolant through the x-ray system 70 to cool the x-ray generating components 82 and to insulate casing 86 from high electrical charges found within vacuum vessel 90. To cool the coolant to proper temperatures, a radiator (not shown) is provided. Fans (not shown) may also be mounted near the radiator to provide cooling air flow over the radiator as the dielectric oil circulates therethrough. Electrical connections are provided in anode receptacle 92 and cathode receptacle 94 that allow electrons 96 to flow through the x-ray system 70.

Casing 86 is typically formed of an aluminum-based material and lined with lead to prevent stray x-ray emissions. A motor assembly 98 is also provided adjacent to vacuum vessel 90 and within the casing 86. In a preferred embodiment, motor assembly is a radial flux motor. A window 100 is provided that allows for x-ray emissions created within the system 70 to exit the system and be projected toward a subject, such as a medical patient for diagnostic imaging. Typically, window 100 is formed in casing 86. Casing 86 is designed such that most generated x-rays 102 are blocked from emission except through window 100.

Anode 78 includes a rotating, disc-shaped anode disc 104. Upon excitation of an electrical circuit connected to the cathode 80 and the anode 78, electrons 96 which are directed and accelerated towards the anode 78 strike the surface of the anode disc 104 and thereby produce high frequency electromagnetic waves 102 in the x-ray spectrum. The x-rays are then directed out of the x-ray system 70 through transmissive window 100 toward the object. Rotation of the anode disc 104 improves the thermal load of the anode thereby allowing higher tube currents. Higher tube currents enable greater dose availability for data acquisition.

Figure 3:
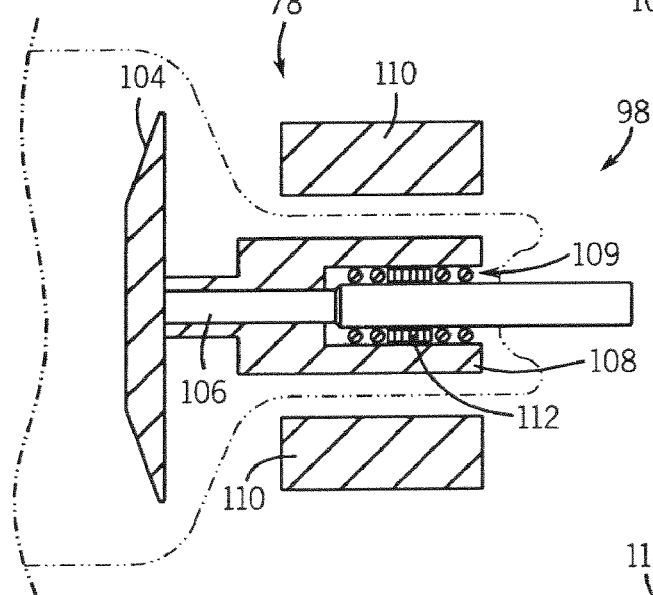
FIG. 3 is a partial cross-sectional view of the anode assembly shown in FIG. 2.

Referring now to FIG. 3, anode 78 includes anode disc 104 that is attached to a rotor 108 and bearings 109 of motor assembly 98 via stem 106. It is preferred that a poor heat conductive material be used to attach the anode disc to the rotor/bearing assembly. Molybdenum is commonly used in rotating anode configurations because of its poor heat conductive characteristics to reduce heat transfer from the anode disc to the bearings. Bearing mounted rotor 108 supports the anode disc 104 within the evacuated x-ray tube. Positioned around the rotor 108, in the illustrated embodiment, is a stator assembly 110 that induces rotation of anode disc 104. The anode disc 104 may be caused to rotate at speeds up to 10,000 revolutions per minute.

Still referring to FIG. 3, anode 78 also includes, in one embodiment, an energy storage device such as a spring 112 operationally connected to rotor 108 and housed within bearing cartridge 109. Spring 112 is attached to the rotor and configured such that energy is stored in the spring when the anode disc 104 is counter-rotated. In this regard, alternating current may be supplied to stator 110 so as to induce counter-rotation of rotor 108. This counter-rotation effectively tightens or stores energy in spring 112.

Prior to data acquisition, the rotor is caused to counter-rotate so as to store energy in spring 112. Once a sufficient amount of energy is stored in the spring, the counter-rotational bias placed on the rotor is removed. As a result, the energy stored in spring 112 is allowed to release thereby causing rotation of rotor 108. Since the motor is turned off and the anode disc is caused to rotate by spring 112 alone, magnetic field disturbances are not caused. Accordingly, MR and x-ray data acquisition may be carried out at higher x-ray dosage levels and with a relatively homogeneous magnetic field. Since most MR scans are completed within 60 minutes, it is preferred that spring 112 be constructed to support a 60 minute rotation of anode disc 104 so that higher dosage levels may be utilized throughout the entire MR data acquisition period.

In another embodiment, anode 78 is constructed without spring 112. In this embodiment, rotation of rotor 108 is caused at a sufficient frequency or revolutions per minute such that once the rotational bias is removed, momentum generated in the rotor 108 will support rotation of the anode disc throughout the imaging exam. For example, anode disc 104 may be caused to rotate at a frequency of 200 Hz. Once a frequency of 200 Hz or higher is reached and maintained, the motor 98 is turned off and thereby is no longer inducing rotation of disc 104. Momentum forces, however, cause continued rotation of the anode disc 104 despite removal of the bias placed thereon by the motor 98. Preferably, the rotor and bearing assemblies are constructed such that the wind-down time of the anode disc 104 is approximately sixty minutes or the length of a conventional MR scan.

Figure 4:
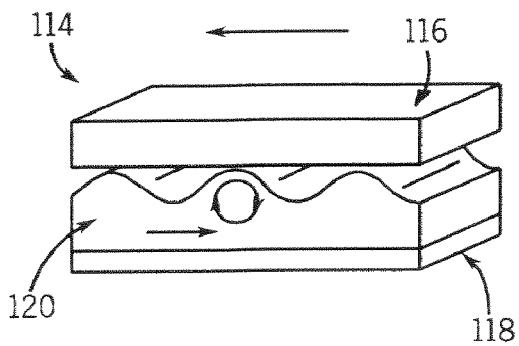
FIG. 4 is a perspective view of a piezoceramic motor for use with the present invention.

Referring now to FIG. 4, a piezoceramic motor that is applicable with the present invention is illustrated. Piezoceramic motor 114 induces rotation in the anode disc without disturbing the relatively homogeneous $B_0$ magnetic field necessary for MR data acquisition. Piezoceramic motor 114 includes a slider component 116 and a piezoceramic vibrator component 118. An elastic vibrator component 120 is sandwiched between slider 116 and piezoceramic vibrator 118. As is generally well known, piezoceramic motors convert voltage and charge to force and motion. In this regard, an alternating current is supplied that through piezoelectric properties induces motion in slider component 116. Slider 116 is operationally connected to the anode stem such that when a sufficient voltage and current is supplied rotation of the anode stem is caused. That is, in a power stroke, the slider disengages the anode stem and, in a thrust stroke, the slider engages the stem and imparts a force thereon. If the power thrust cycle is repeated at a sufficient frequency, rotation of the stem may be caused. One skilled in the art will appreciate that the voltage and current levels may be controlled so as to induce more motion and force in one direction than in another. As a result, rotation of the anode disc in a desired direction may be effectively achieved. Further, one skilled in the art will readily recognize that other piezoelectric or ultrasonic motors may be equivalently applicable with the present invention.

Therefore, in accordance with one embodiment of the present invention, an imaging system is disclosed that includes an MR imaging apparatus to acquire MR data of a subject as well as an x-ray imaging apparatus having a rotatable anode integrally disposed in the MR imaging apparatus to acquire radiographic data of the subject.

In accordance with another embodiment of the present invention, an MR apparatus is disclosed that includes an MR imaging system having a plurality of gradient coils positioned about a bore of a magnet to impress a polarizing magnetic field and an RF transceiver system and an RF switch controlled by a pulse module to transmit RF signals to an RF coil assembly to acquire MR images. The MR apparatus further includes a motor assembly configured to control rotation of a rotatable anode disposed in the bore of the magnet.

According to another embodiment of the present invention, a method of diagnostic imaging includes the steps of impressing a substantially homogeneous magnetic field about a subject and projecting high frequency electromagnetic energy at the subject. The method further includes the steps of rotating an anode of a high frequency electromagnetic energy tube assembly in the magnetic field during the projecting, and acquiring MR and radiographic data from the subject.

The present invention has been described in terms of the preferred embodiment, and it is recognized that equivalents, alternatives, and modifications, aside from those expressly stated, are possible and within the scope of the appending claims.

What is claimed is:

1. An imaging system comprising:
   a magnetic resonance (MR) imaging apparatus to acquire MR data of a subject;
   an x-ray imaging apparatus having a rotatable anode integrally disposed in the MR imaging apparatus to acquire radiographic data of the subject; and
   a motor assembly configured to rotate the anode in a magnetic field generated in a magnet bore of the MR imaging apparatus during data acquisition, wherein the motor assembly includes a radial flux motor and a biasing spring operationally connected to the anode such that rotation of the anode by the radial flux motor biases the spring in a stored energy condition and wherein the spring is further configured to rotate the anode when the bias placed on the spring is removed such that the motor assembly does not induce flux in the magnetic field during data acquisition.

2. The imaging system of claim 1 wherein the motor assembly includes a non-magnetic flux motor.

3. The imaging system of claim 2 wherein the non-magnetic flux motor includes a piezoceramic motor.

4. The imaging system of claim 1 wherein the motor assembly includes a radial flux motor designed to rotate the anode at a specified frequency before MR data acquisition.

5. The imaging system of claim 4 wherein the anode is configured to rotate in the magnet bore from the specified frequency to a slower frequency without a force applied thereon by the radial flux motor during MR data acquisition.

6. The imaging system of claim 1 wherein the MR imaging apparatus includes a split-coil MR magnet.

7. An MR apparatus comprising:
   a magnetic resonance imaging (MRI) system having an x-ray tube assembly to generate an x-ray beam for radiographic data acquisition, and further having a plurality of gradient coils positioned about a bore of a magnet to impress a polarizing magnetic field and an RF transceiver system and an RF switch controlled by a pulse module to transmit RF signals to an RF coil assembly to acquire MR data; and a motor assembly configured to control rotation of a rotatable anode of the x-ray tube assembly disposed in the bore of the magnet, wherein the motor assembly includes a radial flux motor configured to rotate the rotatable anode to a pre-data acquisition rotational speed and disengage from the rotatable anode during a simultaneous acquisition of radiographic and MR data such that the rotatable anode rotates during the simultaneous acquisition of radiographic and MR data as a result of momentum generated in the rotatable anode before the simultaneous acquisition of radiographic and MR data.

8. The MR apparatus of claim 7 wherein the motor assembly includes a piezoccramic drive motor.

9. A method of diagnostic imaging comprising the steps of:
impressing a substantially homogeneous magnetic field about a subject;
projecting high frequency electromagnetic energy at the subject;
rotating an anode of a high frequency electromagnetic energy tube assembly in the magnetic field during the projecting;
acquiring MR and radiographic data from the subject; and
wherein the step of rotating includes the step of counter-rotating the anode prior to data acquisition to store energy in a spring connected to the anode and thereafter removing a bias placed on the anode to allow the spring to release the stored energy during data acquisition.

10. The method of claim 9 further comprising the step of causing the anode to rotate at approximately 200 Hz after the bias is removed.

11. The method of claim 9 including the step of counter-rotating the anode with a radial flux motor.

12. A magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images;

a motor assembly configured to control rotation of a rotatable anode disposed in the bore of the magnet, wherein the motor assembly further includes an energy storage device operationally connected to the anode and wherein the motor assembly is further configured to counter-rotate the anode so as to store energy in the energy storage device.

13. The MRI system of claim 12 wherein the energy storage device includes a spring.

* * * * *

UNITED STATES PATENT AND TRADEMARK OFFICE
CERTIFICATE OF CORRECTION

PATENT NO.   : 6,973,162 B2
DATED        : December 6, 2005
INVENTOR(S)  : Block et al.

It is certified that error appears in the above-identified patent and that said Letters Patent is hereby corrected as shown below:

Column 9,
Line 16, delete "piezoccramic" and substitute -- piezoceramic --.

Signed and Sealed this

Seventh Day of February, 2006

JON W. DUDAS
*Director of the United States Patent and Trademark Office*